(12) United States Patent
Winqvist et al.

(10) Patent No.: US 8,852,581 B2
(45) Date of Patent: Oct. 7, 2014

(54) TREATMENT OF INFLAMMATORY BOWEL DISEASE

(75) Inventors: Ola Winqvist, Uppsala (SE); Magnus Thorn, Uppsala (SE)

(73) Assignee: ITH Immune Therapy Holdings AB, Soderkoping (SE)

( * ) Notice: Subject to any disclaimer, the term of this patent is extended or adjusted under 35 U.S.C. 154(b) by 1224 days.

(21) Appl. No.: 12/065,047

(22) PCT Filed: Aug. 22, 2006

(86) PCT No.: PCT/SE2006/000959
§ 371 (c)(1),
(2), (4) Date: Aug. 26, 2008

(87) PCT Pub. No.: WO2007/027132
PCT Pub. Date: Mar. 8, 2007

(65) Prior Publication Data
US 2009/0311228 A1 Dec. 17, 2009

(30) Foreign Application Priority Data
Aug. 31, 2005 (SE) ...................................... 0501916

(51) Int. Cl.
*A61K 35/26* (2006.01)
*C12N 5/0783* (2010.01)
*A61K 35/12* (2006.01)

(52) U.S. Cl.
CPC .............. *A61K 35/26* (2013.01); *C12N 2501/25* (2013.01); *C12N 2501/24* (2013.01); *A61K 2035/124* (2013.01); *C12N 2501/51* (2013.01); *C12N 2501/515* (2013.01); *C12N 2501/23* (2013.01); *C12N 2501/10* (2013.01); *C12N 5/0636* (2013.01); *C12N 2501/15* (2013.01)
USPC ...................................................... 424/93.71

(58) Field of Classification Search
None
See application file for complete search history.

(56) References Cited

U.S. PATENT DOCUMENTS

| | | | |
|---|---|---|---|
| 2002/0034500 A1 | 3/2002 | Levings et al. | |
| 2002/0090357 A1 | 7/2002 | Barrat et al. | |
| 2004/0191235 A1 | 9/2004 | Groux et al. | |
| 2011/0081649 A1 | 4/2011 | Thoern et al. | |

FOREIGN PATENT DOCUMENTS

| EP | 1 408 106 A1 | 4/2004 |
|---|---|---|
| EP | 1408106 A1 | 4/2004 |
| WO | WO-03/059264 A1 | 7/2003 |
| WO | WO 04/001073 A1 | 12/2003 |
| WO | WO-2004/050706 A2 | 6/2004 |
| WO | WO 2005/009339 A2 | 2/2005 |
| WO | WO-2005//070090 A1 | 8/2005 |
| WO | WO 2005/070090 A2 | 8/2005 |
| WO | WO 2007/010406 A2 | 1/2007 |
| WO | WO 2007/027132 | 3/2007 |
| WO | WO 2007/133147 A1 | 11/2007 |
| WO | WO 2009/017444 | 2/2009 |

OTHER PUBLICATIONS

Mottet et al. (J Immunol 2003;170;3939-3943).*
Makita et al. (The Journal of Immunology, 2004, 173: 3119-3130).*
Coombes et al. (Immunological Reviews 2005 vol. 204: 184-194).*
Fuss et al. (J. Clin. Invest. 113:1490-1497 (2004)).*
Kruisbeek et al. (Current Protocols in Immunology, Proliferative Assays for T cell Function, pp. 3.12.1-3.12.20, John Wiley & Sons (2004)).*
Andersson, Patrick—Authorized Officer. Swedish, International Search Report for PCT Application No. PCT/SE2006/000959, *ISA/Swedish Patent Office*, pp. 1-8, Apr. 12, 2006,
Bouma et al., The Immunological and Genetic Basis of Inflammatory Bowel Disease, *Nature Reviews*, vol./Iss: 3 (7), pp. 521-533, Jul. 1, 2003.
Derisi et al., Use of cDNA microarray to Analyse Gene Expression Patterns in Human Cancer, *Nature Genetics*, vol./Iss: 14(4), pp. 457-460, Dec. 14, 1996.
Duchmann et al., Tolerance Exists Towards Resident Intestinal Flora but is Broken in Active Inflammatory Bowel Disease (IBD), *Clin. Exp. Immunol.*, vol./Iss: 102, pp. 448-455, Jan. 1, 1995.
Ekbom et al., Ulcerative Colitis and Colorectal Cancer, *New England Journal of Medicine*, vol./Iss: 323 (18), pp. 1228-1233, Nov. 1, 1990.
Garcia de Teba et al., Active Crohn's Disease Patients Show a Distinctive Expansion of Circulating Memory CD4+CD45RO+CD28null T Cells, *Journal of Clinical Immunology*, vol./Iss: 24 (2), pp. 185-196, Mar. 1, 2004.
Wittig et al., The Gut as an Organ of Immunology, Int. J. Colorectal Dis., vol./Iss: 18 (3), pp. 181-187, May 1, 2003.
Hove et al., Marked Difference of CD4+CD45RBhigh Expression by Gut Derived T Lymphocytes in Crohn's Disease and Ulcerative Colitis; Differential Cytokine Synthesis of CD45RB Subpopulations, *Gastroenterology*, vol./Iss: 120 (5), pp. 2674, Jan. 1, 2001.
Lapidus et al., Incidence of Crohn's Disease in Stockholm County 1955-1989, *Gut.*, vol./Iss: 41 (4), pp. 480-486, Jan. 1, 1997.
MacDonald et al., Recent Developments in the Immunology of Inflammatory Bowel Disease, *Scand. J. Immunol.*, vol./Iss: 51 (1), pp. 2-9, Jan. 1, 2000.
Polko et al., Importance of Determination of Lymphocytes in Intestinal Mucosa Biopsy Speciments Using Flow Cytometry in the Evaluation of Ulcerative Colitis Activity, *Vnitr Lek.*, vol./Iss: 48 (3), pp. 197-201, Jan. 1, 2002.

(Continued)

*Primary Examiner* — Zachary Skelding
(74) *Attorney, Agent, or Firm* — Ian J. Griswold; Johnson, Marcou & Isaacs, LLC (57) ABSTRACT

A method of treating inflammatory bowel disease (IBD) comprises collecting regulatory T cells in an activated or non-activated state from a patient's sentinel lymph nodes draining bowel segments with or without IBD, optionally activating the cells by contacting them with a cytokine and an antigen extract obtained from an inflamed bowel segment, expanding the T cells in vitro, and re-infusing the expanded T cell to the patient. Also disclosed are methods for obtaining sentinel nodes, for expanding T cells, for re-establishing the $T_H1/T_H2$ balance in the patient suffering from Crohn's disease, and corresponding uses of the expanded T cells, the cytokine and of antigen extract, as well as of correspondingly activated and expanded T cells.

13 Claims, 4 Drawing Sheets

(56) References Cited

OTHER PUBLICATIONS

Rahbar et al., Evidence of Active Cytomegalovirus Infection and Increased Production of IL-6 in Tissue Specimens Obtained from Patients with Inflammatory Bowel Diseases, *Inflammatory Bowel Diseases*, vol./Iss: 9 (3), pp. 156-161, May 1, 2003.

Sandstrom, Terese—Authorized Officer. Swedish, Internal Search Report for PCT Application No. PCT/SE2008/000464, *ISA/Swedish Patent Office*, pp. 1-7, Apr. 1, 2009.

Schmidt et al., Etiology and Pathogenesis of Inflammatory Bowel Disease, *Minerva Gastroenterol Dietol.*, vol./Iss: 51 (2), pp. 127-145, Jun. 1, 2005.

Strober et al., To be Responsive or Not to be Responsive, That is the Mucosal Question, *Gastroenterology*, vol./Iss: 114 (1), pp. 214-217, Jan. 1, 1998.

Thorn, Magnus, Lymphatic Mapping and Sentinel Node Biopsy: Is the Method Applicable to Patients iwth Colorectal and Gastric Cancer?, *Eur. J. Surg.*, vol./Iss: 166, pp. 775-758, Jan. 1, 2000.

Toms et al., Control of Intestinal Inflammation by Regulatory T Cells, *Microbes and Infection*, vol./Iss: 3 (11), pp. 929-935, Sep. 1, 2001.

Tysk et al., Ulcerative Proctocolitis in Orebro, Sweden: A Retrospective Epidemiologic Study, *Scand. J. Bastroenterol*, vol./Iss: 27 (11), pp. 945-950, Jan. 1, 1992.

Wakefield et al., Crohn's Disease: Pathogenesis and Persistent Measles Virus Infection, *Gastroenterology*, vol./Iss: 108, pp. 911-916, Jan. 1, 1995.

Allez et al., Regulatory T Cells: Peace Keepers inthe Gut, *Inflammatory Bowel Disease*, vol./Iss:10 (5), pp. 666-676, Sep. 1, 2004.

Battaglia et al., Rapamycin Selectively Expands CD4+CD35+FoxP3+ Regulatory T Cells, *Blood*, vol./Iss:105, pp. 4743-4748, Jun. 15, 2005.

Foussat et al., A Comparative Study Between T Regulatory Type 1 and CD4+ CD25+ T Cells in the Immunology, *Journal of Immunology*, vol./Iss:171, pp. 5018-5026, Nov. 15, 2003.

Fuss et al., Disparate CD4+ Lamina Propria (LP) Lymphokine Secretion Profiles in Inflammatory Bowel Disease, *Journal of Immunology*, vol./Iss:157, pp. 1261-1270, Aug. 1, 1996.

Ginzinger, David G., Gene Quantification Using Real-Time Quantitative PCR: An Emerging Technology Hits the Mainstream, *Experimental Hematology*, vol./Iss:30, pp. 503-512, Jun. 30, 2002.

Groux et al., Regulatory T Cells and Inflammatory Bowel Disease, *Immunology Today*, vol./Iss:20 (10), pp. 112-115, Oct. 20, 1999.

Hori et al., Control of the Regulatory T Cell Development by the Transcription Factor Foxp3, *Science*, vol./Iss:299, pp. 1057-1061, Feb. 14, 2003.

Mullin et al., Inflammatory Bowel Disease Mucosal Biopsies Have Specialized Lymphokine mRNA Profiles, *Inflammatory Bowel Diseases*, vol./Iss:2, pp. 16-26, Jan. 1, 1996.

Olson et al., Expanded B Cell Population Blocks Regulatory T Cells and Exacerbates Ileitis in a Murine Model of Crohn Disease, *The J. Clinical Immunol.*, vol./Iss:114 (3), pp. 389-398, Aug. 1, 2004.

Papadakis et al., Expression and Regulation of the Chemokine Receptor CSCR3 on Lymphocytes from Normal and Inflammatory Bowel Diseases, *Inflammatory Bowel Diseases*, vol./Iss:10 (6), pp. 778-788, Nov. 1, 2004.

Saruta et al., Characterization of Foxp3+Cd4+Cd25+ Regulatory T Cells from Mesenteric Lymph Nodes in Human Ulcerative Colitis (UC) (Abstract Only), *Gastroenterology*, vol./Iss:130 (2), pp. 599, Apr. 1, 2006.

Van Deventer, S. J. H., New Biological Therapies in Inflammatory Bowel Disease, *Best Practice & Research Clinical Gastroentarology*, vol./Iss:17, pp. 119-130, Feb. 1, 2003.

Watanabe et al., Hassall's Corpuscles Instruct Dendritic Cells to Induce DC4+CD35+ Regulatory T Cells in Human Thymus, *Nature*, vol./Iss:436, pp. 1151-1155, Aug. 1, 2005.

JP Office Action issued in Appl. No. 2008-528982, *JP Office Action*, pp. 1-10, Feb. 22, 2012.

Bacchetta et al., Growth and Expansion of Human T Regulatory Type 1 Cells are Independent from TCR Activation but Require Exogenous Cytokines, *European Journal of Immunology*, vol./Iss:32, pp. 2237-2245, Aug. 1, 2002.

Goncalves, Mauger, Extended European Search Report issued in Appl. 06769624.5 on Jun. 22, 2012, pp. 1-11, Jun. 8, 2012.

Groux et al., A CD4+ T-cell Subset Inhibits Antigen-Specific T-cell Responses and Prevents Colitis, *Nature*, vol./Iss:389, pp. 737-741, Oct. 16, 1997.

Ishida et al., Generation of Anti-tumour Effector T Cells from Naive T Cells by Stimulation with Dendritic/tumour Fusion Cells, *Journal of Immunology*, vol./Iss:66, pp. 546-554, Nov. 1, 2007.

Ishikura et al., Interleukin-18 Overproduction Exacerbates the Development of Colitis with Markedly Infiltrated Macrophages in Interleukin-18 Transgenic Mice, *Journal of Gastroenterology and Hepatology*, vol./Iss:18, pp. 960-969, Aug. 1, 2003.

Konrad, et al., Immune Sensitization to Yeast Antigens in ASCA-positive Patients with Crohn's Disease, *Inflammatory Bowel Disease*, vol./Iss:10 (2), pp. 97-105, Mar. 1, 2004.

Ouspenski, Ilia I., OA issued in U.S. Appl. No. 12/671,318, pp. 1-7, Jun. 13, 2012.

Weijland, Albert, Extended EPO Search Report issued in Appl. No. 08794093.8, pp. 1-6, Jul. 2, 2010.

English-language translation of Office Action dated Feb. 19, 2013 for Japanese Patent Application No. 2008-528982, 5 pages.

English-language translation of Office Action dated Apr. 30, 2013 for Korean Patent Application No. 10-2008-7007512, 5 pages.

Coombes, J. et al., "Regulatory T Cells and Intestinal Homeostasis," Immunological Reviews, 2005, vol. 204, pp. 184-194.

Foussat, A. et al., "A Comparative Study Between T Regulatory Type 1 and CD4+CD25+ T Cells in the Control of Inflammation," The Journal of Immunology, Nov. 15, 2003, vol. 171, No. 10, pp. 5018-5026.

Makita, S., "CD4+CD25$^{bright}$ T Cells in Human Intestinal Lamina Propria as Regulatory Cells," The Journal of Immunology, Sep. 1, 2004, vol. 173, No. 5, pp. 3119-3130.

Mottet, C. et al., "Cutting Edge: Cure of Colitis by CD4+CD25+ Regulatory T Cells," The Journal of Immunology, 2003, vol. 170, pp. 393-3943.

Papadakis, K. et al., "Expression and Regulation of the Chemokine Receptor CXCR3 on Lymphocytes from Normal and Inflammatory Bowel Disease Mucosa," Inflamm Bowel Dis, Nov. 10, 2004, vol. 10, No. 6, pp. 778-788.

Stokkers, P.C.F et al., "New Cytokine Therapeutics for Inflammatory Bowel Disease," Cytokine 28, 2004, pp. 167-173.

\* cited by examiner

TREATMENT OF INFLAMMATORY BOWEL DISEASE

FIELD OF THE INVENTION

The present invention relates to a method of treating inflammatory bowel disease and a means for carrying out the method.

BACKGROUND OF THE INVENTION

Permanent cures for inflammatory bowel disease (IBD), such as Crohn's disease (CD) and ulcerative colitis (UC), are lacking. In Sweden, 1400 new patients are diagnosed with IBD each year, with the peak incidence at 20 years of age, resulting in life long treatment with cortisone and/or immunosuppressive drugs with severe side effects. Furthermore, IBD often results in surgical bowel resection and permanent stoma, which is a major handicap. Ulcerative colitis also increases the risk of cancer in the large bowel.

IBD is thought to be an autoimmune disease due to abnormalities in the immunological response to normally harmless mucosal antigens. Based on the cytokines involved the inflammation of CD is characterized as a $T_H1$ cell mediated immune response. UC is proposed to have a $T_H2$ cell mediated response, though this has not been clearly shown (Fuss I J et al., 1996. J. Immunol. 157:1261-70; Mullin G E et al., 1996. Inflamm. Bowel Dis. 2:16-26).

Cytokines act as regulators of immunological responses as they stimulate differentiation and proliferation of the cellular elements involved. CD4+ helper T cells may differentiate into two major subpopulations of effector cells, $T_H1$ cells when stimulated by IL-12 and $T_H2$ cells when stimulated by IL-4. $T_H1$ cells secrete IFN-γ that stimulates phagocyte- and cytolytic T cell dependent reactions against intracellular microbes such as viruses or intracellular bacteria. $T_H2$ cells secrete IL-4 and IL-5 that stimulate production of IgE and eosinophil/mast cell mediated defense against parasites. $T_H2$ also functions to down regulate TH1 responses.

OBJECTS OF THE INVENTION

It is an object of the invention to provide a method that cures inflammatory bowel disease or at least keeps it at bay over extended periods of time.

It is another object of the invention to provide a means for use in the method.

Further objects will become apparent from the following summary of the invention, a number of figures illustrating it, the description of preferred embodiments thereof as well from the appended claims.

SUMMARY OF THE INVENTION

The present invention is based on the insight that inflammatory bowel disease, in particular Crohn's disease and/or ulcerative colitis, can be permanently cured or at least kept in a dormant or inactive state by the administration of regulatory T cells (Treg) collected from sentinel nodes of the patient and expanded in vitro. Thereby the inflammation of the bowel is reduced and may be even fully suppressed without having to take recourse to medication such by corticosteroids.

The unresponsiveness of the immune system to orally administered antigens is defined as oral tolerance. Apparently, this mechanism prevents improper immune reaction against intestinal content and is believed to be mediated by at least two processes: first, the activation of regulatory T cells (Tregs, $CD4^+CD25^+$), which are members of the T helper cell family ($CD4^+$), and secondly, the induction of clonal deletion or anergy of T cells. The first process, responsible for the tolerance to low-dose antigen exposure, presumably takes place in the local intestinal lymphoid system and is dependent on the production of the cytokine TGF-β. The second (deletional) process presumably takes place in systemic lymphoid tissue, triggered by filtered antigens, and is similar to the mechanism behind induced tolerance to intravenously administered antigens in the absence of immunological adjuvant. This latter tolerogenic mechanism seems to be more prominent after high-dose antigen exposure.

The activation of T cells is strictly regulated in order to maintain balance in the immune system by avoiding excessive and misdirected immunoresponse as seen in autoimmunity. In patients with Crohn's disease mesenterial lymph nodes are greatly enlarged as a sign of uncontrolled regulation of T cell activation.

As IBD is an inflammation the mesenterial lymph nodes adjacent to the inflammatory site are primarily responsible for the drainage of that site. The first nodes disposed along a direct route from the inflamed area are called sentinel nodes.

According to a first preferred aspect of the invention regulatory T cells in an activated state are collected from a patient's lymph nodes (sentinel nodes) draining bowel segments with IBD, expanded in vitro, and re-infused in the patient.

According to a second preferred aspect of the invention regulatory T cells in a non-activated state are collected from a patient's lymph nodes draining healthy bowel segments that is, bowel segments not affected by IBD, expanded in vitro, and re-infused in the patient. The activated as well as the non-activated regulatory T cells so collected can be (further) activated in vitro by suitable agents such as cytokines.

According to a third preferred aspect of the invention regulatory T cells in an activated state or a non-activated state are collected from lymph nodes draining bowel segments with or without IBD, respectively, and expanded in vitro. Expansion may be continuous or in intervals, such as in phases interrupted by resting phase(s). The expanded regulatory T cells are activated (stimulated) with cytokine(s) in combination with an antigen extract from an inflammatory bowel segment. Alternatively the regulatory T cells collected from lymph nodes draining bowel segments with or without IBD are activated (stimulated) in such manner prior to expansion or between expansion phases. One cytokine, preferably two or more cytokines selected from IL-2, IL-7, IL-10, TGF-β, TSLP, such as a cytokine cocktail comprising IL-2, IL-7, IL-10, TGF-β, in particular TGF-β1, TSLP, are used in combination with the antigen extract from the inflammatory bowel segment to obtain Treg activation. It is also preferred to provide for additional Treg activation by use of anti-CD3, anti-CD28 and rapamycin. After expansion, the expanded and activated regulatory T-cells are re-infused in the patient.

Treatment with autologous regulatory T cells has the advantage of reduced or even lacking side effects, and of high efficacy.

According to a first variant of the third preferred aspect, regulatory T cells in an activated state collected from lymph nodes draining bowel segments with or without IBD from a patient with Crohn's disease, and activated with an antigen extract from the inflammatory site in combination with a low dose of the cytokine IL-2 for expansion, preferably in further combination with antibodies against IFN-γ and/or TNF-α to suppress $T_H1$ skewing and $T_H2$ expansion. It is also preferred to condition the culture medium in intervals such as from every day to every fifth day, in particular every day for a time period of from one week or more, in particular for a time period of from three to four weeks. Thereby a population of $T_H2$ cells is obtained, which is used in autotransfusion to re-establish the $T_H1/T_H2$ balance in a patient. Expansion can be supported by additional activation with a CD3 antibody. To improve $T_H2$ skewing an anti CD28 antibody can additionally be used in the expansion in combination with an anti IL-12 antibody.

According to a second variant of the third preferred aspect, regulatory T cells in an activated state collected from lymph nodes draining bowel segments with or without IBD from a patient with ulcerative colitis disease, are activated with an antigen extract from the inflammatory site in combination with one or more of the cytokines IL-2, IL-12 and IFN-α for expansion, preferably in further combination with anti IL4 and/or anti IL-10 antibodies. It is also preferred to condition the culture medium in intervals such as from every day to every fifth day, in particular every day for a time period of from one week or more, in particular for a time period of from three to four weeks. Additional stimuli such as CD3 and CD28 may be provided, in particular towards the end of the expansion period.

According to a fourth preferred aspect of the invention is provided one or more cytokines in a pharmaceutically acceptable carrier for in-vitro activation of regulatory T cells collected from a patient with IBD, in particular from sentinel nodes affected by IBD.

According to a fifth preferred aspect of the invention is provided a method of obtaining sentinel lymph nodes draining bowel segments with IBD comprising injecting a lymphatic staining agent such as patent blue into lesional areas of the intestine of a patient suffering from IBD, identifying lymphatic tissue stained by the agent, optionally marking the stained tissue by sutures, and resecting the stained tissue. The resected tissue is carefully investigated (inspected, such as by microscopy), whereupon the sentinel lymph nodes draining bowel segments with IBD are excised from the tissue.

According to a sixth preferred aspect of the invention is provided a method of isolating regulatory T cells from a sentinel lymph node draining a bowel segment with IBD, comprising exerting a pressure on the lymph node, collecting the cell suspension thereby expelled from the node, and isolating regulatory T cells from the suspension.

According to a seventh preferred aspect of the invention are provided regulatory T cells isolated from a sentinel lymph node draining a bowel segment with IBD.

Further preferred aspects of the invention are included in the appended claims.

The invention will now be explained in greater detail by reference to preferred but not limiting embodiments of the invention illustrated by a number of figures.

DESCRIPTION OF PREFERRED EMBODIMENTS

Example 1

Identification of Sentinel Nodes Draining Inflammatory Bowel Segments

The sentinel node technique has been used for a decade to establish the staging of malignant tumours, mainly malignant melanoma and breast cancer. The sentinel node is identified during surgery by depicting the lymph drainage from the cancer using a lymphatic staining agent such as patent blue (CAS 129-17-9 and patent blue V (CAS 3536-49-0; often supplied as a calcium-chelated dimer), which is injected in the lesional areas of the intestine. The sentinel nodes so identified are marked by suture(s) or by other means. Then the intestinal lesions together with unaffected marginal zones and mesentery including vessels and regional lymph nodes are resected in a conventional manner. The resected tissue is carefully investigated and the sentinel nodes identified and removed. This method is applied to sentinel nodes draining both inflamed and unaffected intestine in patients with ulcerative colitis or Crohn's disease. In addition a venous blood sample is collected from the patient. The peripheral blood sample and the nodes together with specimens from the inflammatory lesions as well as intestinal segments unaffected by the disease are then processed in the laboratory for immunological analysis and T cell expansion. Peripheral blood leukocytes (PBL) are purified by Ficoll-Hypaque (Pharmacia, Amersham). Single cell suspensions of lymph node cells are obtained by gentle pressure using a loose fit glass homogenizer. Antigen extracts from intestinal samples are prepared by homogenizing the tissue fragments in a Dounce homogenizer, followed by 5 min denaturation at 97° C. The cells are then subjected to functional analyses.

Example 2

Isolation of T Cell Populations

Lymphocytes and monocytes are purified from blood samples or buffy coats using Ficoll-Hypaque Plus (Amersham Biosciences, Uppsala, Sweden). The buffy coat or blood sample in question was diluted with PBS and carefully layered onto Ficoll-sodium diatrizoate solution, after which the two-phase system was centrifuged at 400·g for 30 min. The lymphocytes and monocytes collected at the interphase between the Ficoll solution and plasma, whereas erythrocytes and granulocytes gathered at the bottom of the tubes. The lymphocyte layer was removed using a Pasteur pipette, and the cells washed with HBSS to remove excess Ficoll-Hypaque Plus, plasma and platelets. When the cells were not used immediately, they were stored at 37° C. in RPMI medium containing 10% HuS, 1% PeSt and 1% glutamine. Conventional CD4$^+$Th cells and CD4$^+$CD25$^+$ cells were purified using an autoMACS Separator (Miltenyi Biotec, Bergisch Gladbach, Germany). The cells were counted, centrifuged at 300·g for 10 min, the supernatant pipetted off completely and cells dissolved in 90 µL of MACS buffer (0.5% BSA, 2 mM EDTA, 0.01% sodium azide in PBS) and 10 µL of Biotin-Antibody Cocktail per 10$^7$ cells. This labelled all non-CD4+ cell populations. After 10 min incubation at 4 μC, 20 μL of Anti-Biotin MicroBeads per 10⁷ cells was added and incubated for an additional 15 min at 4° C. Cells were washed with ~20 volumes of MACS buffer, centrifuged at 300·g for 10 min, the supernatant removed completely and the cells re-suspended in 500 μL of MACS buffer per 10⁸ cells. Magnetic separation was carried out in an autoMACS Separator to deplete non-CD4+ cells from the sample. To isolate the CD4+/CD25+ cells from the CD4+ population, the CD4+ cells were counted, centrifuged at 300·g for 10 min, supernatant removed completely and pellet dissolved in 90 μL of MACS buffer and 10 μL of CD25 MicroBeads per 10⁷ cells. After 15 min incubation at 4° C., the cells were washed as described above and the CD25+ cells were isolated by positive selection in the autoMACS Separator. Aliquots from all populations were analyzed by flow cytometry.

Example 3

Characterization of Cells by Flow Cytometry

Flow cytometry (FACS) was used to investigate the expression of different surface markers on the isolated cell populations. Cells were distributed into 4 mL FACS tubes, washed with 2 mL FACS buffer (2% FCS, 0.05% sodium azide in PBS), centrifuged at 300·g for 10 min, the supernatant poured off and the pellet re-suspended in 100 μL of FACS buffer. 7 μL of each antibody to be used was added and incubated for at least 30 min at 4° C. whereupon the cells were washed once more with FACS buffer, centrifuged as before and re-suspended in 1 mL of FACS Lysing Solution for cell fixation and erythrocyte lysis, mixed and incubated for 10 min at 4° C. before washing and centrifuging them once again as described above. The supernatant was poured off and cells re-suspended in 500 μL of FACS buffer per tube, after which analysis was carried out using a Becton Dickinson FACSCalibur instrument (Franklin Lakes, N.J., USA).

Example 4

Proliferation Assays

The suppressive ability of the purified CD4+CD25+ cells was investigated. Round-bottomed 96-well plates were incubated with 25 μL of 5 μg/mL anti-CD3 IgG in PBS at 37° C. for 90 min. Wells were washed three times with 200 μL of PBS after which three different cell populations were added. 100 μL of 500,000 cells/mL CD4-cells radiated with 25 Gy were added to each well together with 30 000 CD4+CD25− responder cells and 1 μg/mL soluble CD28 (final concentration). CD4+CD25+ cells were added to the wells in varying amounts to create a number of different CD4+CD25−/CD4+CD25+ cell ratios. As a control equal numbers of CD4+CD25− cells were added to the responder cells in an additional set of wells.

Plates were kept at 37° C. for four or five days before 1 μCi of [3H]thymidine was added to each well and the plates were incubated for 18 h after which they were frozen at −20° C. The cells were thawed, and the well content transferred to a glass fibre filter (Wallac, Turku, Finland) by a cell harvester (TOMTEC, Hamden, Conn., USA). MeltiLex A—Melt-on scintillator sheets (Wallac, Turku, Finland) were placed on top of the filters and melted at 85° C. Radioactivity was measured using a 1205 Betaplate Liquid Scintillation Counter (Wallac, Turku, Finland).

Example 5

TGF-β1 Induction of FoxP3

CD4+CD25− cells were prepared from buffy coat as described above. PBMCs were prepared from a different donor and radiated (25 Gy). 3·10⁶ CD4+ cells were then allo-activated by 1.25·10⁶ PBMCs in a volume of 2 mL/well in 6-well plates with or without 1 ng/mL TGF-β1. The plates were kept at 37° C. Cell samples were taken for flow cytometry analysis and RNA extraction on day 2, 5 and 7.

Example 6

RNA Extraction and cDNA Synthesis

RNA extraction from different cell populations for later use in PCR assays was performed as follows. Cells were lysed in 1 mL of TRIzol (Invitrogen, Carlsbad, Calif., USA) per 5-6·10⁶ cells, after which the sample was either immediately frozen at −70° C. for storage or incubated 5 min at room temperature before 0.2 mL of chloroform per mL TRIzol reagent was added and the tubes shaken vigorously. After 2-3 min the tubes were centrifuged at 12,000·g for 15 min at 4° C. The transparent, aqueous phase was transferred to a fresh tube, the RNA precipitated with 0.5 mL of isopropanol per mL TRIzol used in a first step and incubated 10 min at room temperature before centrifugation at 12,000·g for 10 min at 4° C. The supernatant was removed and the pellet washed with 1 mL of 75% ethanol per mL TRIzol used in the first step. Tubes were vortexed and centrifuged at 7,500·g for 5 min at 4° C., after which the pellets were briefly air-dried (5-10 min), dissolved in 10 μL of RNAse free water and incubated at 55° C. for 10 min. cDNA synthesis was carried out with iScript cDNA Synthesis Kit (Bio-Rad, Hercules, Calif., USA) according to the manufacturer's protocol.

Example 7

Polymerase Chain Reaction (PCR) and Real Time Quantitative PCR

Synthesized cDNA from the different cell populations was used in PCR. The aim with the PCR was to detect expression of FoxP3, GAPDH and RNA polymerase II (RPII) Primers were obtained from Cybergene AB, Huddinge, Sweden. Sequences:
FoxP3, forward—CAGCACATTCCCAGAGTTCCTC (SEQ ID NO: 1), reverse—
GCGTGTGAACCAGTGGTAGATC (SEQ ID NO: 2);
GAPDH, forward—
GAAGGTGAAGGTCGGAGTC (SEQ ID NO: 3),
reverse—GAAGATGGTGATGGGATTTC (SEQ ID NO: 4);
RPII, forward—
GCACCACGTCCAATGACAT (SEQ ID NO: 5), reverse—
GTGCGGCTGCTTCCATAA (SEQ ID NO: 6). For ordinary PCR ThermoPol Reaction Buffer and Taq DNA polymerase (New England Biolabs, Frankfurt am Main, Germany) was used whereas iQSYBR Green Supermix (Bio-Rad, Hercules, Calif., USA) was used in quantitative real time PCR. The reactions were carried out in MyCycler Thermal Cycler or iCycler iQ Real-Time PCR Detection System (Bio-Rad, Hercules, Calif., USA) respectively, according to the protocol: 30 s at 95° C., 30 s at 48-65° C. and 30 s at 72° C. for at least 40 repetitive cycles. For the quantitative real-time PCR reactions a relative quantitation method was applied as reviewed by Ginzinger D G, Exp.

Hematol. 2002 30:503-12. PCR products were separated on a 2% agarose gel, and bands detected by UV excitation of incorporated ethidium bromide.

Example 8

Investigation of Tregs Obtained from Sentinel Nodes of IBD Patients

Figure 1:
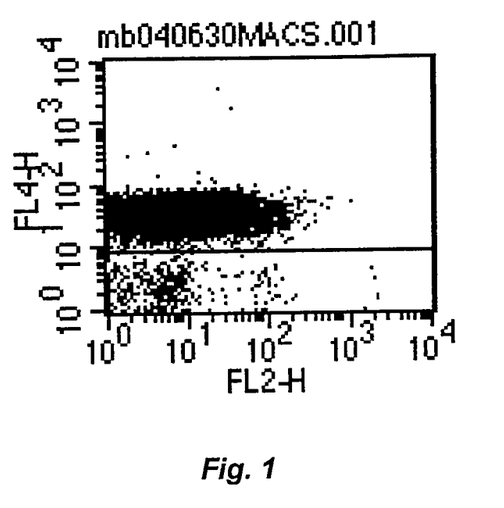
FIG. 1 is a diagram showing activated Tregs in a Treg sample identified by the expression of two surface markers.

Sentinel nodes from a total of 20 patients with IBD were harvested by surgery and investigated. Sentinel node acquired lymphocytes (SEALs) were characterized with respect to the expression of surface markers CD4, CD8, CD3, the T cell receptor (TCR), CD25, CD69, CD45RA, CD45RO and CD14. The number of $CD4^+CD25^{hi}$ Treg population was examined (FIG. 1). The number of Treg cells was found to be normal in sentinel nodes draining an inflammatory bowel segment, compared to the number of Tregs in sentinel nodes draining non-affected areas of the intestine.

Figure 2:
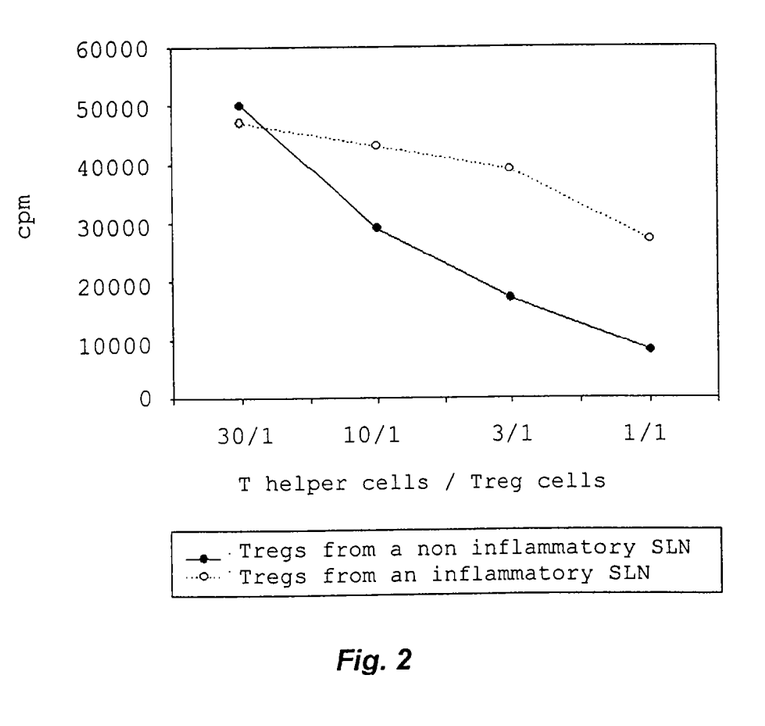
FIG. 2 is a diagram showing a functional Treg assay.

Tregs ($CD4^{+CD}25^{hi}$) purified from sentinel nodes draining an inflammatory segment and Tregs ($CD4^{+CD}25^{hi}$) purified from a bowel segment not engaged in the inflammation however differed substantially in their regulatory activation of T cells: the Tregs from sentinel nodes draining the inflammatory site performed unsatisfactory in regulating the activation of T cells (FIG. 2). In other words, the T cell response regulating capability of Tregs from sentinel nodes draining affected areas is clearly impaired.

Example 9

Expansion of Regulatory T Cells

Figure 3:
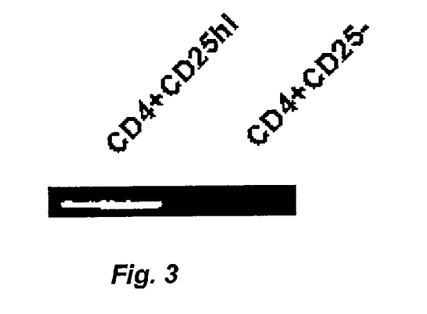
FIG. 3 shows an RT-PCR assay of mRNA extracted from expanded Tregs.

For Treg induction and expansion $CD4^+CD25^-$ T cells from peripheral blood were stimulated with IL-2, CD28, allogenic feeder cells and TGF-β. After expansion >85% of CD4+ T cells expressed high levels of CD25 indicating Treg phenotype as investigated by FACS (not shown). RT-PCR demonstrated that the expanded population contained the Treg hallmark transcript FoxP3, which was not present in the $CD4^+CD25^-$ population prior to expansion (FIG. 3).

Figure 4:
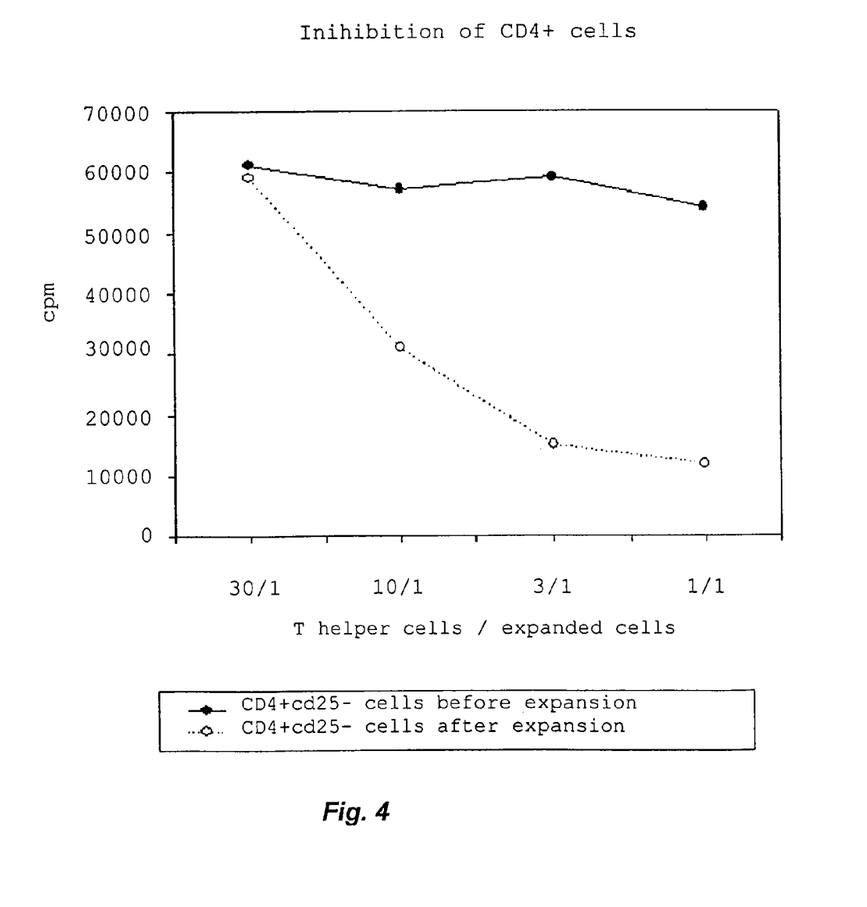
FIG. 4 is a diagram showing the regulating capacity of a Treg population before and after expansion.

The induced and expanded Treg population was tested functionally to demonstrate its capability to inhibit T cell activation. The expanded $CD4^+CD25^+FoxP3^+$ population (FIG. 3) exhibited Treg regulatory properties as demonstrated by its inhibition of T helper cell proliferation already at a 1:10 ratio (FIG. 4). The number of Tregs seems to be normal in sentinel nodes draining inflammatory bowel segments from patients with IBD; they appear to be inefficient in inhibiting the response of stimulated T cells. By stimulating and expanding naïve T cells efficient T regulatory properties can be accommodated.

Example 10

Figure 5:
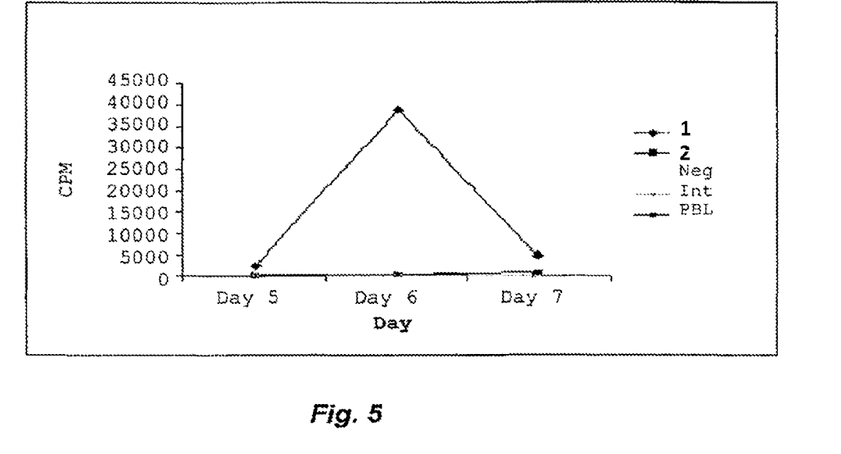
FIG. 5 is a diagram showing the activation of human immunological cells by an endogenous extract from an inflamed bowel section.

Recognition of Antigens Derived from the Inflammatory Site by Regulatory T Cells Derived from Sentinel Nodes Regulatory T cells derived from sentinel nodes, negative nodes, intestinal epithelia and peripheral blood leukocytes were incubated in different concentrations of intestinal cell homogenates for five to seven days. Proliferation was observed for Tregs from sentinel nodes stimulated with antigen extract from an inflammatory area (FIG. 5).

However, when regulatory T cells derived from sentinel nodes were stimulated with antigen extracts derived from non-inflammatory sites no or very week responses were seen (not shown). Findings from patients with Crohn's disease were similar to those from patients with ulcerative colitis.

Figure 6:
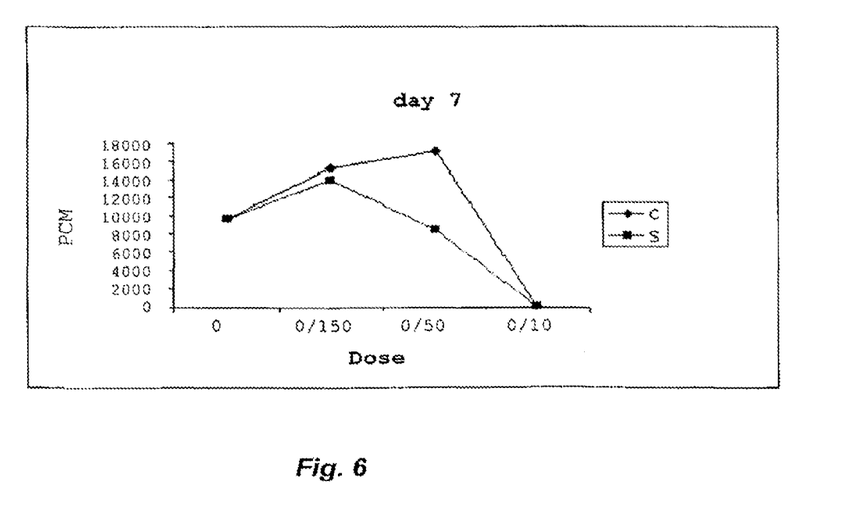
FIG. 6 is a diagram showing the dose response of similarly activated Tregs derived from sentinel nodes.

Sentinel nodes draining affected areas in the caecum and in the sigmoid colon both recognize and proliferate against the same antigen extract derived from the inflammatory site (FIG. 6). The findings indicate that there is a common antigen responsible for clonal expansion of T cells. The high spontaneous proliferation observed is due to in vivo clonal T cell expansion in the sentinel node. Regulatory T cells derived from a sentinel node respond in proportion to the dose of antigen extract.

Figure 7:
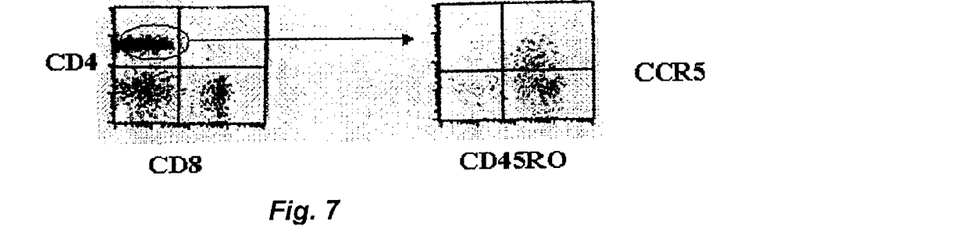
FIG. 7 shows the expression of CCR5 as a marker for $T_H2$.

Regulatory T cells derived from sentinel nodes display an increased expression of cytokines. $CD4^+$ T cells from sentinel nodes are $CD45RO^+/CCR5^+$ in patients with UC suggesting a state of exaggerated $T_H2$ inflammatory response against the inflammatory mucosa (FIG. 7).

Figure 8:
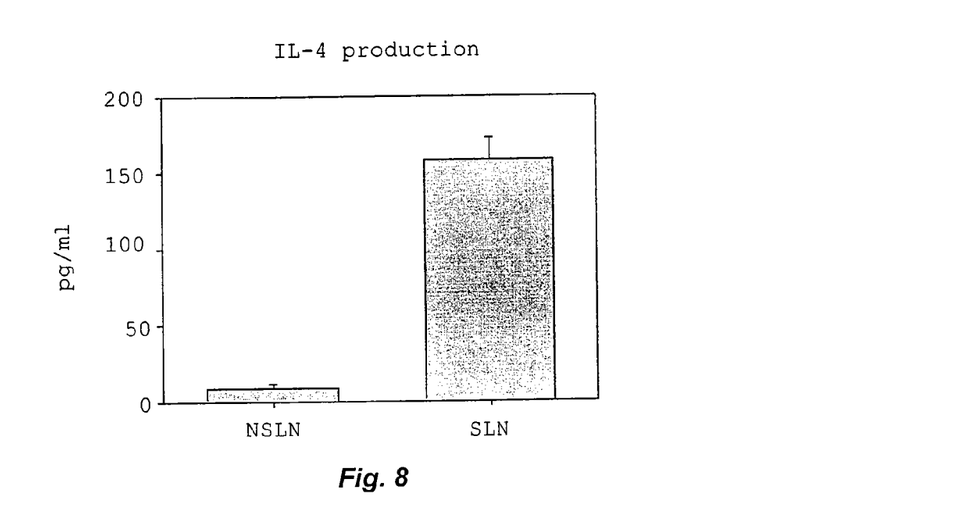
FIG. 8 shows the secretion of IL-4 in Tregs from UC patients.

Sentinel nodes from patients with UC secrete increased amounts of IL-4, a Th2 cytokine, upon activation with an antigen extract from the inflammatory site (FIG. 8).

Figure 9:
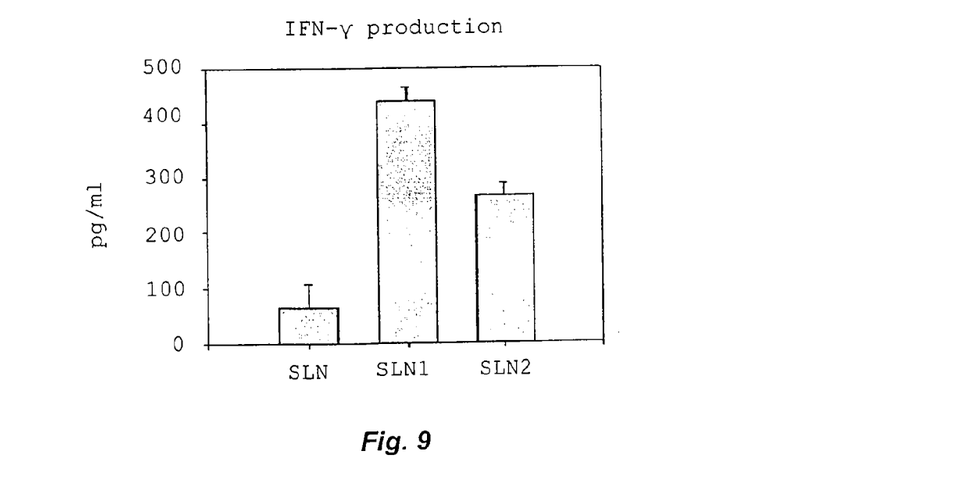
FIG. 9 shows the secretion of IFN-γ in Tregs from CD patients.

Regulatory T cells derived from sentinel nodes from patients with Crohn's disease respond with an increased production of the $T_H1$ cytokine IFN-γ upon antigen specific activation (FIG. 9).

The findings indicate that T cells derived from sentinel nodes from patients with UC have an exaggerated proliferative response against antigens from the inflammatory site and that the regulatory T cells derived from sentinel nodes react with a $T_H2$ response as suggested by the increased CCR5 expression (FIG. 7) and increased production of $T_H2$ cytokines such as IL-4 (FIG. 8). T cells derived from sentinel nodes from patients with Crohn's disease display an opposite pattern of activation with predominantly production of $T_H1$ cytokines such as IFN-γ.

Endothelial cells from the ulcer in UC or the inflammatory site in the intestine of patients with UC or Crohn's disease go into apoptosis or necrosis and are then endocytosed by professional antigen presenting cells (APC). APC endocytose disintegrated endothelial cells and migrate via lymphatic vessels to the draining lymph node, the sentinel node, where APC processes and present proteins (antigens) derived from the endothelial cells to T cells. The T cells become activated, undergo clonal expansion and leave the lymph node to seek areas of inflammation were they become effector cells and contribute to the inflammation.

Example 11

Treatment of IBD

IBD, in particular Crohn's disease and/or ulcerative colitis, can be treated by harvesting regulatory T cells from sentinel nodes of a patient draining the inflammatory area, expanding them and activating them in vitro, and giving them back to the patient by infusion. In particular, in vitro expansion of regulatory T cells in an antigen specific manner takes advantage of clonally expanded Tregs accumulated in sentinel nodes. Treg from sentinel nodes from patients with IBD are expanded under GMP conditions and activated using a cytokine cocktail containing IL-2, IL-7, IL-10, TGF-β together with antigen extract from the inflammatory bowel segment to achieve antigen specific expansion of Tregs. The efficacy of activation is evaluated with RT-PCR, FACS and in vitro inhibition assays as described (FIG. 4). Additional activation with anti-CD3, anti-CD28 and rapamycin can be used to obtain optimal expansion and functionality of the IBD Tregs. Alternatively, if the Tregs from sentinel nodes draining an inflammatory bowel segment are not satisfactory in regard of their number and/or function, expansion of Tregs from sentinel nodes draining non-inflammatory segments using the same protocols is considered. The rationale behind this alternative approach is that one may consider a non-inflammatory segment being appropriately regulated, thus the Tregs are functional although too few in number to maintain regulation in adjacent bowel segments. Expanded Tregs of either kind are given back as an auto-transfusion to reinstate orderly immunoregulation.

LEGENDS TO FIGURES

FIG. 1. Tregs identified by the expression of surface markers CD4+ and high level of the IL-2 receptor CD25, CD4+ CD25$^{hi}$.

FIG. 2. Functional Treg assay. Purified Tregs from sentinel nodes draining an inflammatory intestinal segment (open circles) and a non-inflammatory segment (filled circles) were incubated with CD4+CD25− T helper cells purified from peripheral blood and activated with anti CD3 and anti CD28. 3H Thymidine was added to the cultures during the final 16 hours.

FIG. 3. Expansion of Treg cells. CD4+CD25− cells were activated with IL-2, TGF-β, anti-CD28 and feeder cells in order to stimulate expansion of Treg cells. mRNA was extracted from expanded CD4+CD25+ Tregs and the FoxP3 transcript was demonstrated by RT-PCR, identifying the expanded population as Treg.

FIG. 4. Regulation of stimulated responder T helper cells. A pre-expansion population containing CD4+CD25− cells is unable to regulate (filled circles) whereas adequate regulation is obtained by expanded CD4+CD25+ cells (open circles).

FIG. 5. Activation of human immunological cells. Cells obtained from sentinel lymph nodes (1), non-sentinel lymph nodes (2), the intestine (Int) as well as peripheral blood lymphocytes (PBL) were activated by an endogenous antigen extract derived from an inflamed bowel section of an ulcerative colitis patient.

FIG. 6. Dose response diagram. The dose response of regulatory T cells derived from sentinel nodes draining the caecum and the sigmoid colon, activated by an endogenous antigen extract derived from the same inflammatory bowel section, is shown.

FIG. 7. Expression of CCR5 as a marker for $T_H2$. Regulatory T cells derived from sentinel nodes from a patient with UC have elevated expression of CCR5 on CD4+ CD45RO+ memory cells as a sign of TH2 activation.

FIG. 8. Secretion of the $TH_2$ cytokine IL-4 in regulatory T cells from patients with UC. Cells from non-sentinel nodes (nSLN) and from sentinel nodes (SLN) were stimulated for 48 h with inflammatory antigen extracts. Secreted IL-4 was measured in cultured supernatants using sandwich ELISA.

FIG. 9. Secretion of the $T_H1$ cytokine IFN-γ by regulatory T cells derived from sentinel nodes from patients with Crohn's disease. Cells from non-sentinel nodes (nSLN) and from sentinel nodes (SLN1 and SLN2) were stimulated for 48 h with an inflammatory antigen extract. Secreted IFN-γ was measured in cultured supernatants using sandwich ELISA.

The invention claimed is:

1. A method of treating inflammatory bowel disease (IBD) in a human patient, comprising:
    injecting a lymphatic staining agent into lesional areas of an intestine of a human patient suffering from IBD, identifying lymphatic tissue stained by the agent as sentinel lymph node draining bowel, isolating regulatory T cells from the sentinel lymph nodes, expanding the collected T cells in vitro in culture medium, contacting the collected T cells with one or more cytokines in combination with an antigen extract obtained from an inflamed bowel segment before, concurrently or after expansion, and re-infusing the expanded T cells to the patient.

2. The method of claim 1, wherein the inflammatory bowel disease is Crohn's disease.

3. The method of claim 1, wherein the inflammatory bowel disease is ulcerative colitis.

4. The method of claim 1, wherein the one or more cytokine is selected from the group consisting of IL-2, IL-7, IL-10, TGF-β1, and TSLP.

5. The method of claim 1, further comprising activation of the collected T cells by anti-CD3, anti-CD28 or rapamycin or a combination thereof.

6. The method of claim 1, further comprising conditioning the culture medium at periodic intervals.

7. The method of claim 1, further comprising activation of the collected T cells by an anti CD28 antibody in combination with an anti IL-12 antibody.

8. The method of claim 1, wherein the regulatory T cells are activated by contacting them with an antigen extract obtained from the inflammatory site in combination with one or more of a cytokine selected from the group consisting of IL-2, IL-12 and IFN-α.

9. The method of claim 8, wherein additional activation is effected by contacting the regulatory T cells with CD3 or CD28 or both.

10. The method of claim 1, further comprising (a) additionally activating the regulatory T cells with antigen extract from an inflammatory site in combination with a cytokine IL-2; (b) expanding the cells; and (c) optionally contacting the cells during expansion with antibody against IFN-γ or TNF-α or both to suppress TH1 skewing and TH2 expansion, whereby the TH1/TH2 balance in a patient is rebalanced.

11. The method of claim 10, further comprising conditioning of the culture medium in intervals.

12. The method of claim 11, further comprising stimulating expansion by contacting the cells with a CD3 antibody.

13. The method of claim 1, wherein the lymphatic staining agent is patent blue.

* * * * *

SEQUENCE LISTING

```
<160> NUMBER OF SEQ ID NOS: 6

<210> SEQ ID NO 1
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
cagcacattc ccagagttcc tc                                             22

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gcgtgtgaac cagtggtaga tc                                             22

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gaaggtgaag gtcggagtc                                                 19
```

-continued

```
<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gaagatggtg atgggatttc                                                 20

<210> SEQ ID NO 5
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gcaccacgtc caatgacat                                                  19

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gtgcggctgc ttccataa                                                   18
```